(12) United States Patent
Fan et al.

(10) Patent No.: US 9,008,797 B2
(45) Date of Patent: Apr. 14, 2015

(54) IN-LINE CONNECTOR TERMINALS FOR IMPLANTABLE MEDICAL ELECTRICAL LEADS

(71) Applicant: Medtronic, Inc., Minneapolis, MN (US)

(72) Inventors: Yaling Fan, Savage, MN (US); Douglas N Hess, Maple Grove, MN (US); Megan M Kruse, Shoreview, MN (US); Nathan Lee Olson, Shoreview, MN (US); Kathryn R Parsons, Fridley, MN (US); Vu D Tran, Blaine, MN (US); Gareth Morgan, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/061,313

(22) Filed: Oct. 23, 2013

(65) Prior Publication Data

US 2014/0052228 A1 Feb. 20, 2014

Related U.S. Application Data

(62) Division of application No. 13/051,096, filed on Mar. 18, 2011, now Pat. No. 8,567,055.

(51) Int. Cl.
*A61N 1/08* (2006.01)
*A61N 1/05* (2006.01)
*H01R 43/20* (2006.01)

(52) U.S. Cl.
CPC . *A61N 1/05* (2013.01); *H01R 43/20* (2013.01)

(58) Field of Classification Search
None
See application file for complete search history.

(56) References Cited

U.S. PATENT DOCUMENTS

2005/0221671 A1 * 10/2005 Lyu et al. ..................... 439/587

* cited by examiner

*Primary Examiner* — Brian T Gedeon
*Assistant Examiner* — Ankit Tejani
(74) *Attorney, Agent, or Firm* — Michael C. Soldner (57) ABSTRACT

An implantable medical electrical lead includes a plurality of conductors that extend continuously, without any intermediary junctions, between a plurality of electrodes and a corresponding plurality of contact members of an in-line connector terminal. A junction between each conductor and the corresponding contact member is preferably formed by first fitting a conductive sleeve, which is coupled to a proximal portion of the conductor, into an eyelet feature of the contact member, which is mounted on a strut member, and then welding the sleeve to the contact member at a pre-formed slot of the contact member, which extends along an external recessed surface thereof. The assembly of the connector terminal preferably completes the construction of the lead, wherein the proximal portion of each conductor is positioned in a helical path, which extends between an elongate body of the lead and the connector terminal, and along which a grip zone is formed.

8 Claims, 6 Drawing Sheets

IN-LINE CONNECTOR TERMINALS FOR IMPLANTABLE MEDICAL ELECTRICAL LEADS

RELATED APPLICATION

This application is a divisional of U.S. patent application Ser. No. 13/051,096, filed Mar. 18, 2011 entitled "IN-LINE CONNECTOR TERMINALS FOR IMPLANTABLE MEDICAL ELECTRICAL LEADS", herein incorporated by reference in its entirety.

TECHNICAL FIELD

The present invention pertains to implantable medical electrical leads, and more particularly to assemblies of in-line connector terminals thereof.

BACKGROUND

Many implantable medical devices include a connector bore with which a connector terminal of an implantable medical electrical lead may mate, via insertion therein, in order to electrically couple electrodes, and/or other active sensing or therapy delivery members of the lead, with power and control circuitry contained in the device. The typical implantable medical electrical lead includes an elongate insulative body within which insulated conductors extend, wherein the conductors couple sensing or therapy delivery members, mounted on the lead body, to contact members of the connector terminal. Each contact member of the lead connector terminal electrically engages with a corresponding device contact within the device connector bore when the lead connector terminal is fully inserted therein.

Numerous configurations of implantable medical electrical lead connector terminals have been disclosed over the years, many of which are directed toward compliance with international industry standards that specify essential dimensions and performance requirements to assure compatibility of connection between device connector bores and lead connector terminals among a variety of manufacturers. The most recently developed international standard, ISO/FDIS 27186: 2009(E), dictates the form for a four-pole in-line connector terminal of cardiac pacing and defibrillation leads and is commonly known as the IS-4 (or DF-4) standard. Commonly-assigned U.S. Pat. Nos. 7,108,549 and 7,241,180 disclose lead connector terminal embodiments that may comply with the IS-4 standard. Although these disclosures, as well as others, define various configurations and arrangements of structural elements and electrical connections that accommodate the construction of an implantable medical electrical lead with an integral multi-pole in-line connector terminal, there is still a need for improved designs and associated assembly methods.

SUMMARY

In preferred embodiments and according to preferred methods of the present invention the construction of an implantable medical electrical lead is completed with the assembly of an in-line connector terminal, wherein each contact member of the connector terminal is coupled at a proximal junction by a corresponding conductor of a plurality of elongate conductors that extend continuously from the proximal junctions to distal junctions with electrodes of the lead, without any splices/intermediary junctions; and, preferably, in completing the construction of the lead, a proximal portion of each conductor is positioned in a helical path, about which a grip zone is formed. According to some embodiments, each proximal junction is formed by fitting a conductive sleeve, which has been conductively coupled to a proximal portion of the corresponding conductor, within an eyelet feature of the corresponding contact member, and then forming a weld joint between the fitted conductive sleeve and an external recessed surface of the contact member, wherein the weld joint is located at a pre-formed slot of the contact member and is subsequently overlaid by a corresponding insulator member of the in-line connector.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions and manufacturing processes are provided for selected elements, and all other elements employ that which is known to those skilled in the field of the invention. Those skilled in the art will recognize that some of the examples may have suitable alternatives. Although some preferred embodiments of the present invention comply with the aforementioned IS-4 standard, as generally illustrated herein, the invention is not so limited.

Figure 1:
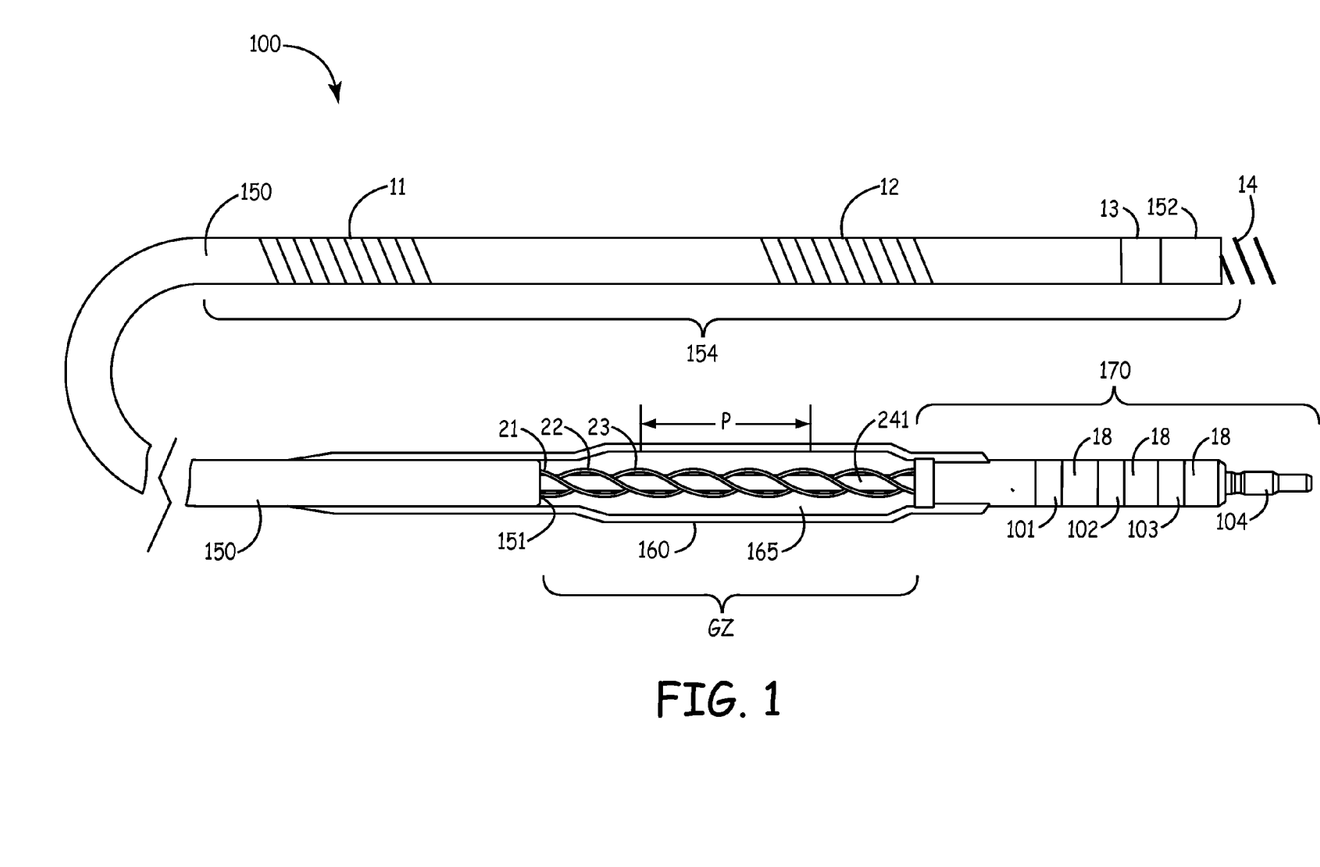
FIG. 1 is a plan view of an implantable medical electrical lead, including a partially cut-away section, according to some embodiments of the present invention.

FIG. 1 is a plan view of an implantable medical electrical lead 100, including a partially cut-away section, according to some embodiments of the present invention. FIG. 1 illustrates lead 100 including a plurality of electrodes 11, 12, 13, 14, which are mounted to a distal portion 154 of an elongate insulative lead body 150, and an in-line connector terminal 170 extending proximally from a proximal end 151 of body 150. FIG. 1 further illustrates a cut-away section along a grip zone GZ of lead 100, through which a plurality of elongate conductors 21, 22, 23 extend in a helical path, from proximal end 151 of body 150 to connector terminal 170, for example, in order to provide strain relief when grip zone GZ is subjected to bending/flexing forces; the helical path of conductors 21, 22, 23 wraps about an insulative tubing 241 in which another conductor 24 (FIG. 2) extends. A length of grip zone GZ may be between approximately 1 inch and approximately 2.5 inches, and a maximum pitch P of the helical path is, preferably, no greater than approximately 1 inch. According to the illustrated embodiments, in addition to providing a location for gripping, in order to insert connector terminal 170 into a medical device connector bore, grip zone GZ provides a transition in bending flexibility between the relatively flexible elongate lead body 150 and the relatively stiff connector terminal 170. Although FIG. 1 illustrates grip zone GZ bridged by an insulative sleeve 160 that encloses a space 165, for example, filled with an insulative bulk of material surrounding conductors 21, 22, 23, 24, the insulative bulk of grip zone GZ may be continuous to the external surface thereof, such that a separate sleeve is not necessary according to alternate embodiments. Alternative methods for forming grip zone GZ will be described below. Lead body 150 and the insulative materials of grip zone GZ may be formed from medical grade silicone rubber or polyurethane, or combinations thereof, according to methods known in the art.

With further reference to FIG. 1, in-line connector terminal 170 includes a plurality of contact members 101, 102, 103, preferably rings, and a contact pin 104 which are spaced apart and isolated from one another by a plurality of insulator members 18. According to some exemplary embodiments, connector terminal 170 conforms to the aforementioned IS-4 standard, which dictates, among other things, the external dimensions of connector terminal 170 as a whole, as well as those of each contact 101, 102, 103, 104 and each insulator 18. However, it should be noted, that alternate embodiments of the present invention need not conform to the IS-4 standard. Those skilled in the art will appreciate that each contact 101, 102, 103, 104 of connector terminal 170 electrically engages with a corresponding implantable medical device contact in a connector bore of the device, when connector terminal 170 is fully inserted within the bore. According to the illustrated embodiment, electrodes 11 and 12 are adapted to deliver high voltage therapy, and electrodes 13 and 14 are adapted to deliver low voltage therapy (i.e. pace and sense); conductors 21, 22, 23, 24 are electrically coupled to electrodes 11, 12, 13, 14, respectively, and extend proximally from the couplings, within lead body 150, being isolated from one another, for example, by containment within individual lumens formed in body 150. The couplings, or junctions, between conductors 21, 22, 23, 24 and corresponding electrodes 11, 12, 13, 14 may be formed by any suitable method known in the art. Contact pin 104 is electrically and mechanically coupled to tip electrode 14 via central conductor 24, which extends within tubing 241 and lead body 150, preferably, directly from a junction with contact pin 104 to a junction with electrode 14, such that pin 104 may be rotated to extend and retract electrode 14, out from and back into a distal end 152 of lead body 150. Conductor 24 is preferably in the form of a coil, for example, in order to transfer the requisite torque to extend and retract electrode 14. According to some preferred embodiments, conductor 24 and tubing 241 extend within a centrally located lumen 30 (FIG. 4A) of connector terminal 170, so will hereinafter be designated "central conductor". Contact members 101, 102, 103 are also electrically and mechanically coupled, via corresponding conductors 21, 22, 23, to corresponding electrodes 11, 12, 13, and since each of conductors 21, 22, 23 extends peripherally of conductor 24 within grip zone GZ and connector terminal 170, conductors 21, 22, 23 will hereinafter be designated "peripheral conductors". Peripheral conductors 21, 22, 23 each preferably have a jacket, or coating of insulation extending thereover, to further isolate conductors 21, 22, 23 from one another, wherein the insulation is stripped away at either end of each conductor 21, 22, 23 to create junctions with the corresponding electrode 11, 12, 13 and contact member 101, 102, 103. According to exemplary embodiments, wires of each of conductors 21, 22, 23, 24 are formed from MP35N alloy, which is known in the art, with or without silver cores, and each conductor 21, 22, 23 preferably includes a plurality of relatively fine wire strands that are bundled in a cable configuration, according to methods known in the art, with a coating of fluoropolymer insulation, such as ethylene tetrafluoroethylene (ETFE), extending thereover.

According to preferred embodiments of the present invention, peripheral conductors 21, 22, 23 extend continuously, that is, without any splicing, from distal junctions with respective electrodes 11, 12, 13 to proximal junctions with respective contact members 101, 102, 103, in order to form individual electrical circuits that have no intermediary junctions. The absence of intermediary junctions between those that couple contacts 101, 102, 103 and electrodes 11, 12, 13 to corresponding conductors 21, 22, 23 makes lead 100 inherently more reliable and less costly to manufacture, for example, because a fewer number of parts and assembly operations are necessary. However, the elimination of such intermediary junctions poses some challenges in the assembly of lead 100, which challenges are overcome by the embodiments and methods of the present invention.

Figure 2:
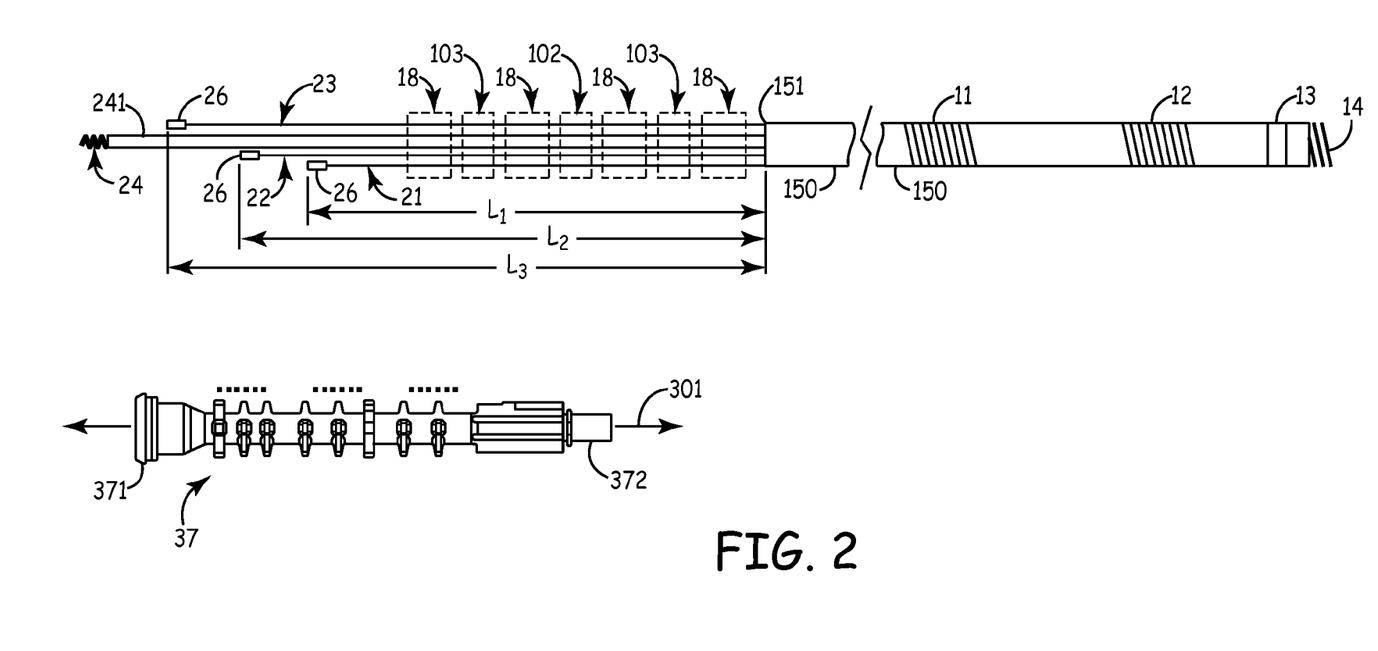
FIG. 2 is a plan view of portions of the lead of FIG. 1, prior to completion of the assembly of an in-line connector, according to some methods of the present invention.

FIG. 2 is a plan view of portions of lead 100, prior to completion of the assembly of in-line connector 170, according to some methods of the present invention, wherein the assembly of in-line connector 170 around a relatively rigid and insulative strut member 37 thereof, is a final stage in the assembly of lead 100 to complete the construction thereof. FIG. 2 illustrates lead body 150 having electrodes 11, 12, 13, 14 mounted to distal portion 154, and proximal portions of elongate conductors 21, 22, 23, 24 extending from a proximal end 151 of lead body 150, each conductor having been coupled to the corresponding electrode 11, 12, 13, 14 in a previous step of the assembly process. FIG. 2 further illustrates the proximal portion of each peripheral conductor 21, 22, 23 having been trimmed to a different length $L_1$, $L_2$, $L_3$, also in a previous step, and a conductive sleeve 26 that is conductively coupled, for example, by crimping, to the proximal terminal end of each peripheral conductor 21, 22, 23, from which a portion of the aforementioned insulation jacket, if included, had been removed, such that each coupled sleeve 26 is in conductive contact with the corresponding conductor 21, 22, 23. According to the illustrated embodiment, the lengths $L_1$, $L_2$, $L_3$ of the proximal portions of peripheral conductors 21, 22, 23 correspond to individual positions of corresponding contact members 101, 102, 103 along strut member 37, as generally indicated with dotted lines, when a gap g (FIGS. 4A-B) is established between a distal end 137 of strut member 37 and proximal end 151 of lead body 150, in a subsequent assembly step. According to some preferred methods, described below, each conductive sleeve 26, which is coupled to the proximal portion of the corresponding peripheral conductor 21, 22, 23, is coupled to the corresponding contact member 101, 102, 103, after the contact member is mounted onto strut member 37.

Figure 4A:
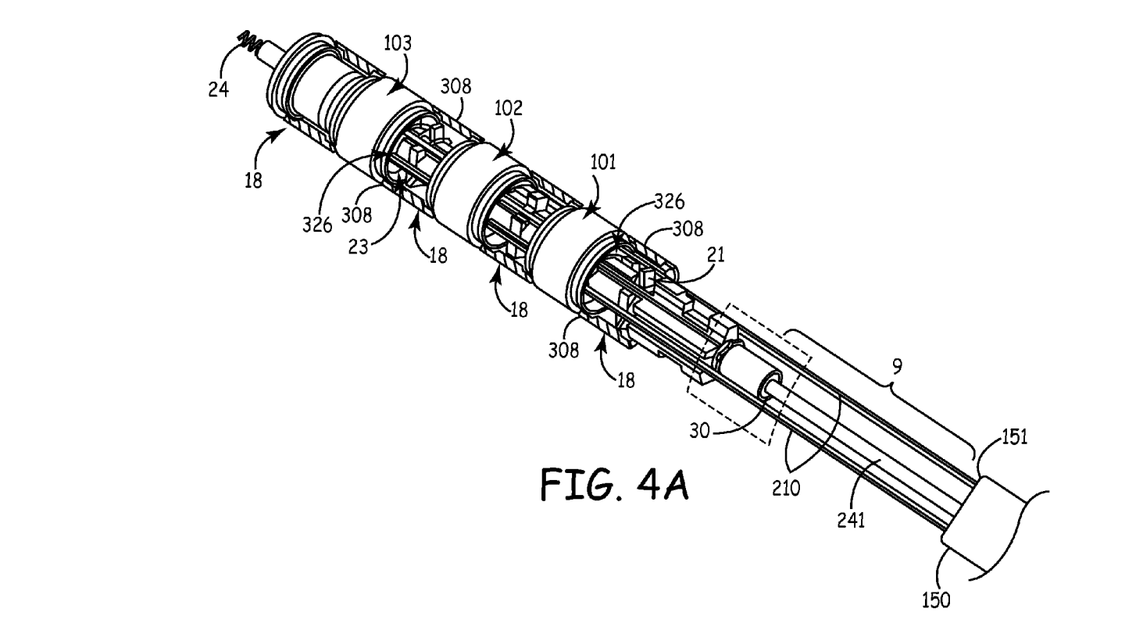
FIG. 4A is a perspective view of a portion of an in-line connector with partial cut-away sections, according to some embodiments.

With further reference to FIG. 2, strut member 37 includes a plurality of protrusions extending from an outer surface thereof, which are configured to support the plurality of contact members 101, 102, 103 and the plurality of insulator members 18, when mounted thereon as illustrated in FIGS. 1 and 4A. According to some preferred embodiments, the features of strut member 37 are similar to those described for a strut (300) of a connector terminal (30) in commonly-assigned U.S. Pat. No. 7,108,549, which is hereby incorporated by reference. Thus, contact members 101, 102, 103 and insulator members 18, when mounted on strut member 37, may be supported by strut member 37 in a fashion similar to that described for the connector terminal in the '549 patent. According to some preferred methods of the present invention, contact members 101, 102, 103 and insulator members 18 are loosely mounted around the proximal portions of conductors 21, 22, 23, 24 in an alternating fashion, for example, as illustrated with dashed lines, and then central conductor 24 may be inserted through a lumen 30 (FIG. 4A) of strut member 37 to loosely hold strut member 37 in position with respect to lead body 150 for the subsequent assembly of connector terminal 170, as will be described in greater detail below. For reference, lumen 30 of strut member 37 generally defines a central longitudinal axis 301 of in-line connector terminal 170.

Figure 3A:
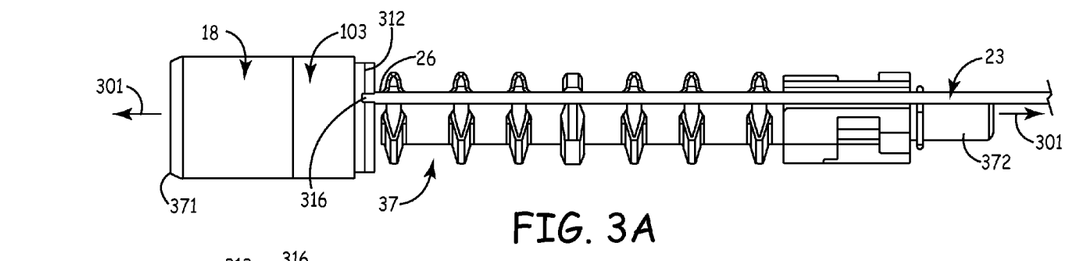
FIG. 3A is a plan view of a portion of an in-line connector, according to some embodiments.
Figure 3B:
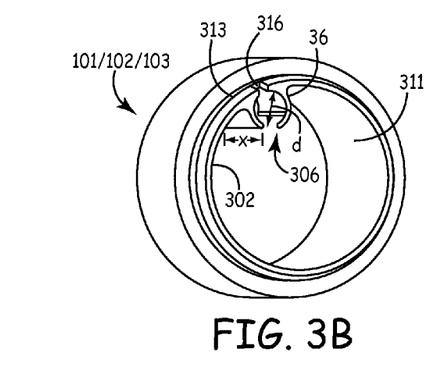
FIG. 3B is a perspective view of a contact member of the in-line connector of FIG. 3A, according to some embodiments.

FIG. 3A is a plan view of strut member 37 on which the proximal-most insulator member 18 and contact member 103 are mounted, and along which the proximal portion of peripheral conductor 23 is routed to form the junction with contact member 103. With reference back to FIG. 2, the remaining contact members 102, 101 and insulator members 18 preferably remain, temporarily, positioned distally away from strut member 37 in order to provide clearance for forming the junction between conductor 23 and contact member 103. According to some preferred embodiments, and with reference to the perspective view of FIG. 3B, each of contact members 101, 102, 103 includes an eyelet feature 36 to receive a fitting of the conductive sleeve 26 of the corresponding peripheral conductor 21, 22, 23 therein as an intermediary step in forming the junction between each conductor and corresponding contact member. FIGS. 3A-B further illustrate contact member 101/102/103 including an external recessed surface 312 and a pre-formed slot 316 formed through member 101/102/103 along surface 312 such that, when conductive sleeve 26 is fitted within eyelet feature 36, a portion of sleeve 26 is exposed through slot 316. With further reference to FIG. 3B, according to some preferred embodiments, external recessed surface 312 of contact member 101/102/103 tapers down to an edge 302 thereof, the significance of which will be described below.

Figure 3C:
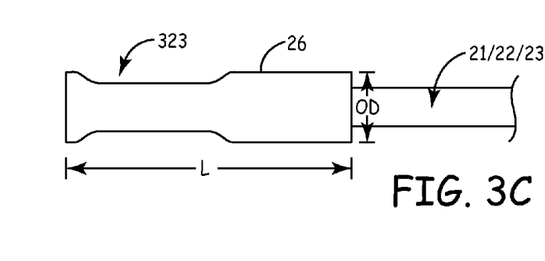
FIG. 3C is a plan view of a conductive coupling that forms a portion of a junction of the in-line connector, according to some embodiments.

FIG. 3B illustrates eyelet feature 36 extending from an inner surface 311 of contact member 101/102/103 and having an inner diameter d and a depth x. FIG. 3C is a plan view of the conductive coupling, for example, a crimp joint 323, between conductive sleeve 26 and peripheral conductor 21/22/23, according to some embodiments. FIG. 3C illustrates an end of conductor 21/22/23 inserted within an inner diameter of sleeve 26 and crimp joint 323 extending along a portion of an overall length L of sleeve 26, for example, approximately 50 to 60% of overall length L. According to an exemplary embodiment, for example, one that employs a cable having an outer diameter of approximately 0.006 inch to 0.007 inch as peripheral conductor 21/22/23, the inner diameter of sleeve is approximately 0.008 inch, an outer diameter OD of sleeve 26 is approximately 0.016 inch and length L of sleeve 26 is approximately 0.05 inch; and inner diameter d of eyelet feature 36 is approximately 0.018 inch and depth x of eyelet feature 36 is approximately 0.05 inch. Sleeve 26 and contact member 101/102/103 may each be formed from stainless steel, or any other suitable biocompatible and biostable conductive material. Crimp joint 323 between sleeve 26 and conductor 21/22/23 may deform an outer perimeter of sleeve 26 such that the fit of sleeve 26 within eyelet feature 36 is a press fit; alternately, or in addition, sleeve 26 and eyelet feature 36 may be sized for a press fit or a line-to-line fit therebetween. In some embodiments, one or both of the outer surface of sleeve 26 and the inner surface of eyelet feature 36 may be tapered for a wedging interface therebetween when sleeve 26 is inserted within eyelet 36. Although eyelet feature 36 is shown having a longitudinally extending opening 306, according to alternate embodiments, opening 306 need not be included. Whether or not opening 306 is present, sleeve 26 is fitted within eyelet feature 36, according to some methods, via insertion in a direction generally parallel with axis 301. Opening 306 may allow for expansion of eyelet inner diameter d about the fitted sleeve 26 and/or may be an access point for pressing sleeve 26 into eyelet feature 36, according to some alternate methods. Sides of eyelet feature 36, on either side of opening 306, can be crimped toward one another after sleeve 26 is fitted therebetween, in order to tighten the fit, according to some methods. In any case, eyelet feature 36 is configured to allow for fitting the conductively coupled sleeve 26 therein and to hold and support the fitted sleeve 26 in place, so that sleeve 26 is exposed through slot 316 for subsequent completion of the proximal junction between conductor 21/22/23 and contact member 201/202/203, for example, by laser welding, as described below in conjunction with FIG. 3D.

Figure 3D:
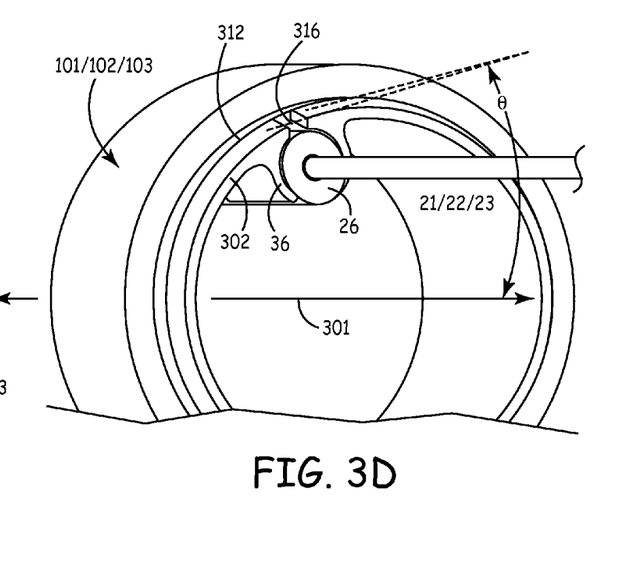
FIG. 3D is an enlarged perspective view of the junction, according to some embodiments.

FIG. 3D, is an enlarged perspective view of the proximal junction, according to some embodiments, wherein conductively coupled sleeve 26 is fitted within eyelet feature 36 so that a weld joint 326 (FIG. 4A) may be formed, between sleeve 26 and contact member 101/102/103, at pre-formed slot 316, where sleeve 26 is exposed. According to some methods, weld joint 326 is formed by directing laser energy toward a portion of external recessed surface 312 of contact member that lies adjacent to slot 316 and, preferably, to edge 302, for example, from a pulsed Nd:YAG (neodymium-doped yttrium aluminium garnet; $Nd:Y_3Al_5O_{12}$) laser source, like the SLS 200 CL8n available from LASAG of Buffalo Grove, Ill., which has been engineered for reliable high precision welding applications. According to some preferred embodiments, and with reference to FIG. 3D, weld joint 326 includes two welds formed by directing the laser energy toward two portions of external surface 312, on opposite sides of slot 316, and along lines that extend at an angle θ of greater than zero degrees and less than ninety degrees with respect to central longitudinal axis 301. According to the illustrated embodiment, external recessed surface 312 preferably tapers down toward edge 302, such that the laser energy is focused on, or in relatively close proximity to the tapering portion of recessed surface 312. According to an exemplary embodiment, a wall thickness of contact member 101/102/103, along external recessed surface 312, tapers from approximately 0.006 inch to approximately 0.003 inch at edge 302. It should be noted that, although strut member 37 is not shown in FIG.

3D, the fitting of sleeve 26 within eyelet feature 316 and the subsequent welding is preferably accomplished when contact member 101/102/103 is mounted on strut member 37, for example, as illustrated in FIG. 3A.

FIG. 4A is a perspective view of partially-assembled in-line connector 170, with partial cut-away sections at each insulator member 18, according to some embodiments. With reference to FIGS. 3A and 4A, after a first of the weld joints 326 is formed between sleeve 26 of conductor 23 and contact member 103, the next adjacent insulator member 18 and contact member 102 are moved into position on strut 37, such that a proximal lip 308 of member 18 overlaps onto the adjacent external recessed surface 312 of contact member 103, thereby overlaying and covering the corresponding weld joint 326. Then sleeve 26 of conductor 22 is fitted within eyelet feature 36 of contact member 102 and welded thereto, at slot 316, after which the next adjacent insulator member 18 and contact member 101 are moved into position on strut 37 so that proximal lip 308 of that insulator 18 overlaps the adjacent external recessed surface 312 of contact member 102 to cover the corresponding weld joint 326, and then the fitting and welding of sleeve 26 is performed to complete the proximal junction of conductor 21 with contact member 101. It should be noted that, according to the illustrated embodiment, a proximal end 371 of strut member 37 includes a pre-formed shoulder that forces distal to proximal mounting of contact members 101, 102, 103 and insulator members 18, when these members are configured as closed rings. However, according to alternate embodiments, in which proximal end 371 of strut member 37 does not include the pre-formed shoulder, the mounting of contact members 101, 102, 103 and insulator members 18 may be accomplished proximal to distal, such that the fitting and welding between conductively coupled sleeves 26 and contact members 101, 102, 103 would be accomplished on an opposite end (proximal as opposed to the illustrated distal) of members 101, 102, 103, and in an opposite order to that described above.

FIG. 4A further illustrates, with dashed lines, a strut end cap which is positioned to be moved over distal end 372 of strut member. The aforementioned '549 patent describes such a strut end cap (311) in detail, as may be employed by embodiments of the present invention, for example, by threading the end cap over each of conductors 21, 22, 23, 24 prior to bringing strut member 37 into position for the above-described creation of the proximal junctions. With further reference to FIG. 4A, according to preferred methods, a proximal end of central conductor 24, which has been inserted through lumen 30 of strut member 37, is coupled to contact pin 104 (FIG. 1), and then pin 104 is attached within proximal end 371 of strut member 37. According to an exemplary embodiment, the interfaces between contact pin 104 and conductor 24, and between contact pin 104 and strut member 37, and between conductor 24 and strut member 37 are similar to those described in the incorporated-by-reference '549 patent.

Figure 4B:
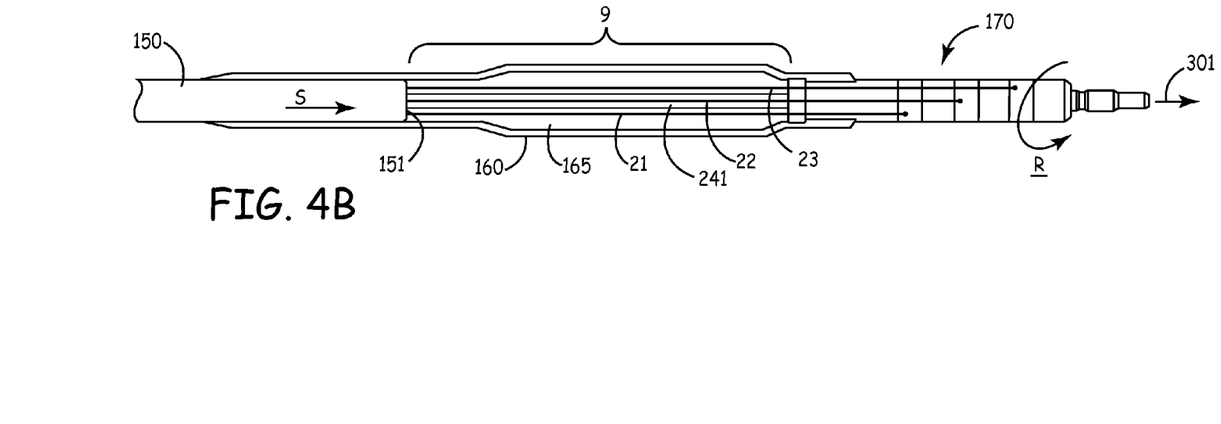
FIG. 4B is a schematic depicting an operation/method step, according to some methods of the present invention.

Turning now to the schematic of FIG. 4B, once connector terminal 170 is assembled, for example, as described above, in conjunction with FIGS. 2-4A, insulative grip sleeve 160 may be loosely positioned to span gap g between proximal end 151 of lead body 150 and distal end 372 of strut member 37. According to some preferred methods, a backfill material is injected into space 165 within grip sleeve 160 that surrounds peripheral conductors 21, 22, 23, and then, before the injected backfill material becomes a cured bulk, assembled connector terminal 170 is rotated, per arrow R, with respect to lead body 150, in order to move the proximal portion of conductors 21, 22, 23 into a helical path around insulative tubing 241 (within which central conductor 24 extends), for example, as illustrated in FIG. 1. It should be noted that, as connector terminal 170 is rotated, lead body 150 is allowed to move (or, alternately, actively moved) toward connector terminal 170, per arrow S, in order to prevent undue stress on conductors 21, 22, 23 and the proximal and distal junctions thereof. Thus, a length of grip zone GZ (FIG. 1) is less than that of gap g. The backfill material injected into space 165 is preferably a silicone medical adhesive that has an uncured viscosity that is not too great, so as to give relatively minimal resistance to the movement of conductors 21, 22, 23 therethrough, and into the helical path. Examples suitable backfill materials include, without limitation, MED1137 and MED1-6540, which have similar viscosities, and the relatively lower viscosity MED2-4213 (viscosity specified at 80,000 centipoise, cP), and LSR-9536-40 (viscosity specified at 26,000 cP), which are all silicone medical adhesives available from NuSil Technology, LLC (headquartered in Santa Barbara, Calif.). According to some alternate methods, conductors 21, 22, 23 are moved into the helical path prior to injecting the backfill material into space 165 within grip sleeve 160. In either case, a support clip (not shown) may be secured around grip sleeve 160, to stabilize grip zone GZ while the backfill material cures. According to some alternate embodiments, an entirety of the insulative bulk of grip zone GZ is integrally formed by insert molding, for example, liquid silicone rubber, around helically extending conductors 21, 22, 23, so that grip sleeve 160 is not necessary. In any case, connector terminal 170 is rotated from approximately 360 degrees to approximately 720 degrees in order to give the helical extent of conductors a maximum pitch of at least approximately 1 inch, when a minimum length of grip zone GZ is approximately 1 inch. As was previously mentioned, the helical extent of conductors 21, 22, 23 provide strain relief thereto, when grip zone GZ is subjected to bending/flexing forces.

Figure 5:
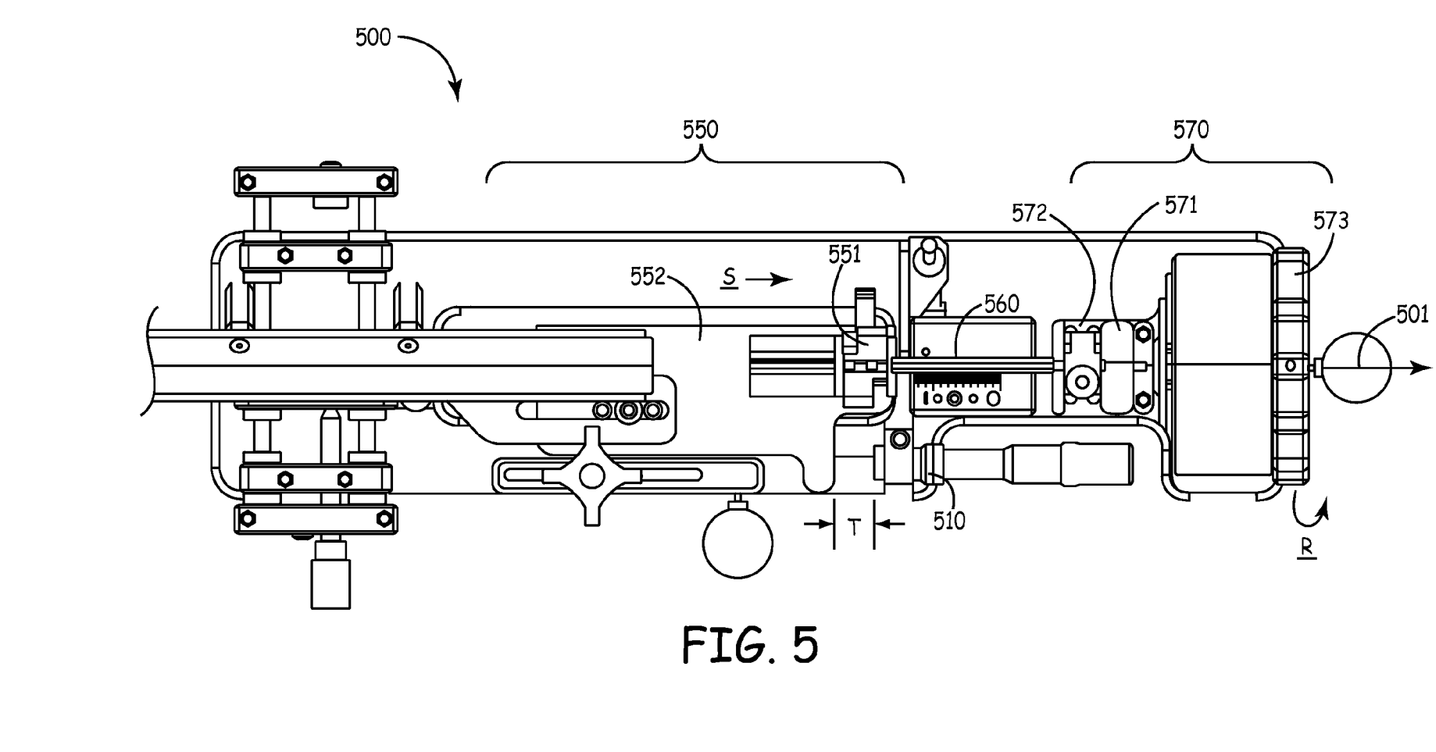
FIG. 5 is a top plan view of a fixture that may be employed, according to some methods.

FIG. 5 is a top plan view of a twist fixture 500 that may be employed to move conductors 21, 22, 23 into the helical path, according to some methods. FIG. 5 illustrates twist fixture 500 including a first support member 570, a second support member 550, and a grip zone guide 560, which extends between first and second support members 570, 550; first support member 570 includes a rotating platform 572 coupled to a dial member 573, and a connector securing member 571 mounted on rotating platform 572. According to FIG. 5, when strut member 37 (with contact members 101, 102, 103 and insulator members 18 mounted thereon and with each peripheral conductor 21, 22, 23 joined to the corresponding mounted contact member) is secured by member 571 to rotating platform 572, and lead body 150, in proximity to proximal end 151, is secured to second support member 550 by a lead body securing member 551, dial member 573 may be turned, per arrow R, to rotate platform 572 about an axis 501, which is substantially aligned with central longitudinal axis 301 of the secured strut member 37 (FIG. 4B), and, thus, rotate the secured strut member 37 with respect to lead body 150. During the rotation, the proximal portions of conductors 21, 22, 23 are moved into the helical path and lead body 150 is drawn proximally toward in-line connector 170, per arrow S; linear movement, per arrow S, is allowed by a floating platform 552 of second support member 550. With further reference to FIG. 5, fixture 500 includes an adjustable stop 510 that may be set, according to the desired length of grip zone GZ, to limit a travel T of platform 552, and thus lead body 150, which is secured to second support member 550 by member 551 during the rotation. Fixture 500 may include a pneumatic drive coupled to second support member 550, as an alternative to a passive floating platform 552. Those skilled in the art of machine design will appreciate that motors and/or pneumatic drives may be employed by twist fixture 500 to automatically control rotation, per arrow R, and linear movement, per arrow S, according to pre-programmed parameters that are set to achieve a desired pitch P of the helical path and a desired length of grip zone GZ (FIG. 1).

Figure 6A:
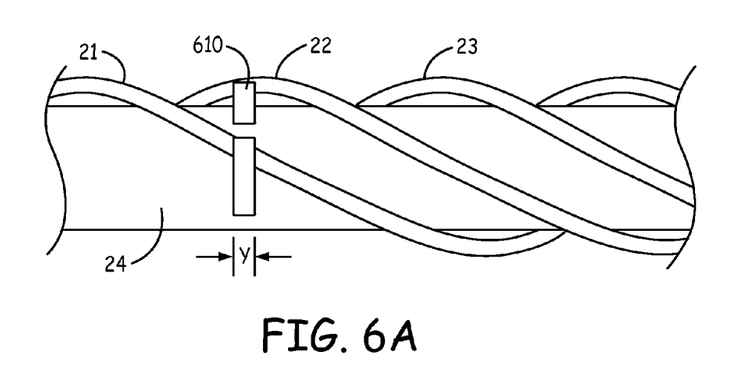
FIG. 6A is a plan view of a portion of a grip zone of the medical electrical lead, according to some embodiments.
Figure 6B:
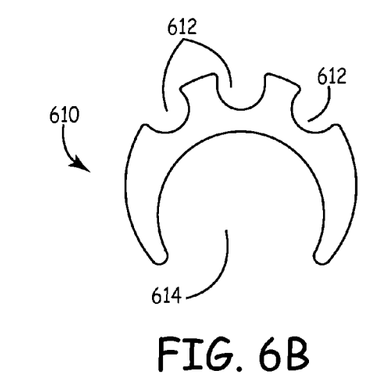
FIG. 6B is an end view of a holding member employed in the grip zone of FIG. 6A, according to some embodiments.
Figure 7A:
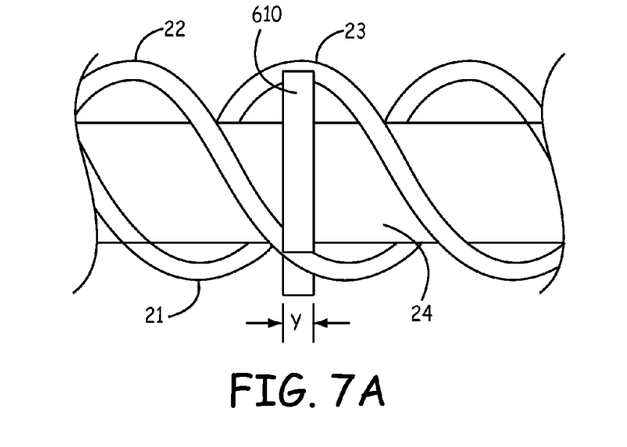
FIG. 7A is a plan view of a portion of a grip zone, according to some alternate embodiments.
Figure 7B:
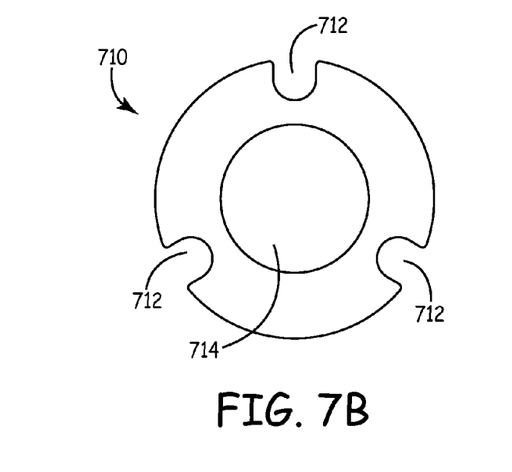
FIG. 7B is an end view of an alternate embodiment of a holding member.

FIG. 6A is a plan view of a portion of grip zone GZ of medical electrical lead 100, according to some embodiments, wherein one or more holding members 610 are employed to hold conductors 21, 22, 23 in the helical path; and FIG. 6B is an end view of holding member 610, according to some embodiments. FIG. 6A illustrates holding member 610 mounted around insulative tubing 241 and each of conductors 21, 22, 23 held within a corresponding open channel 612 of holding member 610, which may be better seen in FIG. 6B. FIG. 6B illustrates a central channel 614 of holding member 610, being sized and positioned for the mounting thereof around tubing 241, and open channels 612 that are longitudinally aligned with one another and arranged about a perimeter of central channel 614 to accommodate a particular arrangement of conductors 21, 22, 23 as they exit proximal end 151 of lead body 150, according to some embodiments. FIG. 7A is a plan view of a portion of grip zone GZ, according to some alternate embodiments, wherein an alternate embodiment of a holding member 710 is employed to hold conductors 21, 22, 23 in the helical path. FIG. 7B, which is an end view of holding member 710, illustrates holding member 710 including open channels 712 that are longitudinally aligned with one another and arranged 120 degrees apart about a perimeter of a central channel 714, which is sized to receive tubing 241 for mounting thereon, as illustrated in FIG. 7A. The arrangement of open channels 712 accommodates a preferred arrangement of conductors 21, 22, 23 as they enter strut member 37 of in-line connector 170, and may also accommodate the arrangement of the conductors as they exit proximal end 151 of lead body, according to some alternate embodiments. Thus, it may be appreciated that, according to some embodiments, at least one of each of holding members 610, 710 may be employed in grip zone GZ to transition conductors 21, 22, 23 from a first arrangement, in proximity to proximal end 151 of lead body (FIG. 6A), to a second arrangement (FIG. 7A) for entry into in-line connector terminal 170. Alternately, one or more of holding members 710 may be employed as illustrated in FIG. 7A without any of holding members 610. According to an exemplary embodiment, holding members 610, 710 are formed from medical grade silicone rubber and have a thickness Y of approximately of approximately 0.03 inch.

According to some methods, as an alternative to the methods described above for moving conductors 21, 22, 23 into the helical path along grip zone GZ, each of conductors 21, 22, 23 can be wound into the helical path about tubing 241, after tubing 241 and conductor 24, which extends therein, are inserted through strut member 37, and before each conductor is coupled to the corresponding contact member 101, 102, 103. By these methods, one or more of either or both of holding members 610, 710 may be fixedly mounted to tubing 241 so that sections of conductors 21, 22, 23 can be inserted into respective open channels 614/714 as they are wound about tubing 241. Alternately, each holding member 610/710 may be loosely mounted around tubing 241 and sections of conductors 21, 22, 23 inserted into respective open channels 614/714 prior to winding, in which case, each holding member 610/710 may be rotated about tubing 241 to wind conductors 21, 22, 23, either partially or completely into the helical path, either before or after conductors 21, 22, 23 are coupled to respective contact members 101, 102, 103. Following the winding, each holding member 610/710 may be fixed in place, for example, via an adhesive bond to tubing 241.

Finally, with reference back to FIGS. 2 and 4A, according to some preferred embodiments, each proximal portion of conductors 21, 22, 23 has an insulative tubing member 210, preferably formed from a fluoropolymer, such as polytetrafluoroethylene (PTFE), fitted relatively loosely thereover, for example, overlaying the aforementioned jacket/coating of insulation that is pre-formed over the length of each conductor 21, 22, 23. According to some methods, the proximal portion of each conductor 21, 22, 23 may be inserted within the corresponding tubing member 210 prior to forming the conductive coupling with the corresponding conductive sleeve 26. Each tubing member 210 preferably extends approximately from the corresponding proximal junction with the corresponding contact member 101, 102, 103, within connector terminal 170, to a location within lead body 150 that is in relatively close proximity to proximal end 151, for example, spaced distally from proximal end 151 by a distance between approximately 0.07 inch and approximately 0.1 inch. When incorporated in the construction of lead 100, tubing members 210 are useful to further alleviate a stress and strain that may be imposed upon the proximal portions of peripheral conductors 21, 22, 23 during flexing of grip zone GZ by allowing conductors 21, 22, 23 to move a bit within grip zone GZ, rather than being tightly bound by the surrounding insulative bulk thereof. Tubing members 210 may also provide redundant insulation, for conductors 21, 22, 23 that include the pre-formed insulative coating/jacket, or a primary insulation, if conductors 21, 22, 23 do not include the pre-formed insulative coating/jacket.

In the foregoing detailed description, the invention has been described with reference to specific embodiments. However, it may be appreciated that various modifications and changes can be made without departing from the scope of the invention as set forth in the appended claims.

We claim:

1. An implantable medical electrical lead comprising an elongate insulative body, a plurality of electrodes mounted to a distal portion of the body, an in-line connector terminal extending from a proximal end of the body, and a corresponding plurality of elongate conductors extending within the body between the electrodes and the in-line connector terminal, the in-line connector terminal including a strut member, a contact pin, a plurality of contact members and a corresponding plurality of insulator members, the contact pin terminating a proximal end of the connector terminal and being engaged within a proximal end of the strut member and coupled to a distal-most electrode of the plurality of electrodes by a first conductor of the plurality of elongate conductors, the first conductor extending through a lumen of the strut member, the lumen defining a central longitudinal axis of the in-line connector terminal, and the plurality of contact members and insulator members being mounted on the strut member such that each insulator member is positioned between adjacent contact members, and the improvement comprising:

each contact member being coupled to a corresponding electrode of the plurality of electrodes by a corresponding peripheral conductor of the plurality of elongate conductors, each peripheral conductor extending continuously from a distal junction with the corresponding electrode to a proximal junction with the corresponding contact member of the in-line connector terminal; and each proximal junction being formed by:

a conductive coupling between a conductive sleeve and the corresponding peripheral conductor;

a fitting of the conductive coupling within an eyelet feature of the contact member, the eyelet feature extending from an inner surface of the contact member toward the central longitudinal axis of the connector terminal; and a weld joint between the fitted conductive coupling and an external recessed surface of the contact member, the weld joint being located at a pre-formed slot of the contact member, the pre-formed slot exposing the conductive sleeve of the fitted conductive coupling and extending from an edge of the contact member and along the external recessed surface;

wherein each weld joint is overlaid by a corresponding insulator member of the plurality of insulator members.

2. The lead of claim 1, further comprising a grip zone extending between the elongate body and the in-line connector, and wherein the improvement further comprises each of the peripheral conductors extending along a helical path within the grip zone.

3. The lead of claim 2, further comprising a holding member mounted around the first conductor and including a plurality of open channels, each peripheral conductor being held within a corresponding open channel of the holding member, the open channels being longitudinally aligned with one another and located about a perimeter of the holding member.

4. The lead of claim 2, further comprising a fluoropolymer tubing member positioned over a proximal length of each elongate conductor, each proximal length extending approximately from the corresponding proximal junction, within the in-line connector terminal, to a location, within the elongate body, in relatively close proximity to a proximal end thereof; and wherein each of the peripheral conductors includes a pre-formed insulative jacket that underlies the corresponding tubing member and extends from the corresponding proximal junction to the corresponding distal junction.

5. The lead of claim 1, wherein the fitting of the conductive coupling within the eyelet feature of the contact member comprises a press fit.

6. The lead of claim 5, wherein one or both of the conductive sleeve and the eyelet feature include(s) a tapered surface at an interface therebetween in the fitting.

7. The lead of claim 1, wherein the eyelet feature of the contact member includes a longitudinally extending opening.

8. The lead of claim 1, wherein the weld joint comprises two welds, one formed on either side of the pre-formed slot.

\* \* \* \* \*